United States Patent [19]

Kuhla

[11] 4,081,455
[45] Mar. 28, 1978

[54] 6-AMINO-2,2-DIMETHYL-3-CYANOPENAMS

[75] Inventor: Donald E. Kuhla, Gales Ferry, Conn.

[73] Assignee: Pfizer Inc., New York, N.Y.

[21] Appl. No.: 772,126

[22] Filed: Feb. 25, 1977

Related U.S. Application Data

[62] Division of Ser. No. 691,999, Jun. 2, 1976, abandoned, which is a division of Ser. No. 503,281, Sep. 5, 1974, Pat. No. 3,992,394.

[51] Int. Cl.$^2$ .................. C07D 499/42; C07D 499/00
[52] U.S. Cl. ........................... 260/306.7 R; 260/239.1
[58] Field of Search ...................... 260/239.1, 306.7 R

[56] References Cited

PUBLICATIONS

Chemical Abstracts, vol. 55, Column 11,394(f) (1961).

Primary Examiner—Gerald A. Schwartz
Attorney, Agent, or Firm—Connolly and Hutz

[57] ABSTRACT 6-amino and 6-(N-protected amino)-2,2-dimethyl-3-cyanopenams, intermediates therefor, and a process for the conversion of the 3-cyano penams, by reaction with a source of azide ion in a reaction inert solvent, to 6-amino-and 6-(N-protected amino)-2,2-dimethyl-3(5-tetrazolyl)penams, intermediates for the preparation of antibacterial agents.

4 Claims, No Drawings

6-AMINO-2,2-DIMETHYL-3-CYANOPENAMS

CROSS-REFERENCE TO RELATED APPLICATION

This application is a division of application Ser. No. 691,999 filed June 2, 1976, and now abandoned, which in turn is a division of application Ser. No. 503,281 filed Sept. 5, 1974 and now U.S. Pat. No. 3,992,394.

BACKGROUND OF THE INVENTION

1. Field of the Invention

This invention relates to 6-amino and 6-(N-protected amino)-2,2-dimethyl-3-cyanopenams, to intermediates therefor, and to the use of the 3-cyanopenams as reactants for the preparation of 6-amino-2,2-dimethyl-3(5-tetrazolyl)penams by reaction with a source of azide ion. More particularly, this invention relates to 6-amino- and 6-(N-protected amino)-2,2-dimethyl-3-carbamylpenams, to their use as intermediates for the preparation of corresponding 6-amino- and 6-(N-protected amino)-2,2-dimethyl-3-cyanopenams which, in turn, are converted, by reaction with a source of azide ion, to 6-amino - and 6-(N-protected amino)-2,2-dimethyl-3-(5-tetrazolyl)penams. The latter compounds are valuable intermediates for the preparation of antibacterial agents.

2. Description of the Prior Art

The penicillins a β-lactam class of antibiotics, consist of N-acyl derivatives of 6-amino-2,2-dimethylpenam-3-carboxylic acid. Since the physicochemical and biological properties of the penicillins are largely determined by the nature of the C.6 substituent, chemical modification of the substituents on the penam nucleus has focused on the C.6 position.

Efforts to improve the therapeutic value of the penicillins have also led to chemical modification at the C.3 position. The 3-carboxy group has been converted to a number of other groups such as salts, anhydrides, carbamyl, esters, thioacid, hydroxymethyl, acid azide, isocyanate, carbamates, hydroxamic and nitrile [Khokhlov, et al., Doklady Akad, Sci. Nauk. S.S.S.R. 135, 875–8 (1960); C. A. 55, 11394F (1961)]. A summary of such modifications presented by HamiltonMiller, Chemotherapia, 12, 73–88 (1967).

In addition, the 3-carboxy group has been replaced by formyl [Gottstein et al., J. Org. Chem. 31, 1922 (1966)], acid chloride [Wolfe et al., Can. J. Chem. 46, 2549 (1968)], hydroxy [Heusler, Helv. Chim. Acta, 55, 388 (1972); Sheenan and Brandt, J. Amer. Chem. Soc. 87, 5468 (1965)], diazoketone [Kleiver, Khim. Geterotsikl. Soed. 1966, 702; Ramsey and Stoodley, J. Chem. Soc. (C) 1969, 1319], carboxymethyl [Kleiver loc. cit.], chloroketones (3—COCH$_2$Cl) [Ramsey and Stoodley, Chem. Commun. 1970, 1517], and the N-sulfonylamides (3-CONHSO$_2$Me) [U.S. Pat. No. 3,641,000]. With trivial exceptions of salts, certain easily hydrolyzed esters, and thioacids, all of these changes result in greatly diminished antibacterial activity.

Conversion of the 3-carboxy group of 6-amino- or 6-(N-protected amino)-2,2-dimethylpenam-3-carboxylic acids to a 5-tetrazolyl group has been found to produce penam derivatives of great value as intermediates for antibacterial agents. The compounds have the formula (I):

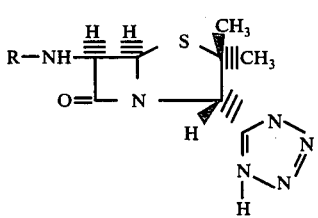

wherein R is selected from the group consisting of hydrogen and amino-protecting group.

The term "amino-protecting group" as used herein is intended to include any group which will permit synthesis of compounds of formula I under the conditions, e.g. of acidity and temperature, of this process and which can be removed under conditions wherein the β-lactam ring remains substantially intact. The nature of the amino-protecting group is not critical to this invention. The R group is not involved in formation of the tetrazolyl moiety. Its function is to protect the amino group and the penam ring system of 6-amino-2,2-dimethyl-3-cyanopenam during the process described in detail below for formation of compounds of formula I. It is subsequently removed at an appropriate point, generally at the ultimate or penultimate step, of the process of this invention at which point its protective function is no longer needed. The selection and identification of individual protecting groups is readily accomplished by one skilled in the art. The suitability and effectiveness of a group as an aminoprotecting group in this invention is simply determined by subjecting the 6-(N-protected-amino)-2,2-dimethyl-3-cyanopenam wherein the protecting group is the group in question to the process of the instant invention. All such groups are to be considered within the scope of this invention.

In general, all groups known, or obvious, in the art as amino-protecting groups in peptide syntheses are operative in the process of this invention. Particular interest resides in the protecting groups enumerated below because of their effectiveness in protecting the 6-amino group and their ease of removal under conditions wherein the β-lactam ring remains substantially intact namely, 2,2,2-trihaloethoxycarbonyl, (e.g. 2,2,2-trichloroethoxycarbonyl, 2,2,2-tribromoethoxycarbonyl) and triphenylmethyl (trityl) groups, especially those of formula II below

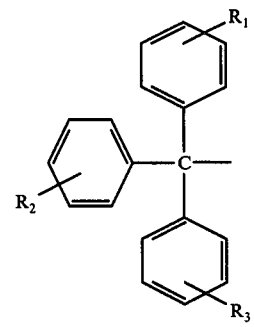

wherein R$_1$, R$_2$, and R$_3$ are each selected from the group consisting of hydrogen, chloro, bromo, fluoro, alkyl having from one to four carbon atoms, alkoxy having from one to four carbon atoms, and phenyl.

When R of formula I is hydrogen, the amino group becomes under the acid conditions of this process, an ammonium ion, and is thus protected.

Additionally, in a broad sense "amino-protecting group" as used herein also embraces acyl moieties of organic carboxylic acids. Special preference is given to 2-phenylacetyl- and 2-phenoxyacetyl groups since these are the acyl groups of penicillin G and penicillin V which serve as convenient precursors to compounds of formula I (see Reaction Scheme I below) wherein R is hydrogen.

The preferred 6-(N-protected amino)-2,2-dimethyl-3-cyanopenams for use in the process of this invention are those wherein R is a triphenylmethyl group (formula II) since such compounds are readily obtained by tritylation of 6-amino-2,2-dimethyl-3-cyanopenam or 6-APA with the appropriate halo derivative of formula II, e.g., triphenylmethyl chloride or bromide. Special preference resides in the triphenylmethyl group as amino-protecting group because of its availability.

The compounds of formula I are valuable intermediates for the synthesis of 6-acylamido-2,2-dimethyl-3-(5-tetrazolyl)penams, an effective class of antibacterial agents, by methods described herein.

For the sake of convenience, the compounds described herein are identified as derivatives of penam. The term "penam" has been defined in the J. Am. Chem. Soc., 75, 3293 (1953), as referring to the structure:

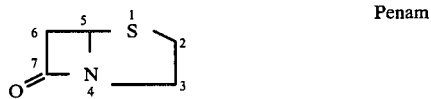

Using this terminology, the well-known antibiotic penicillin G is designated as 6-(2-phenylacetamido)-2,2-dimethyl-penam-3-carboxylic acid. The 3-tetrazolyl surrogate of penicillin G, formula I above wherein R is 2-phenylacetyl, is designated as 6-(2-phenylacetamido)-2,2-dimethyl-3-(5-tetrazolyl)penam.

The 5-substituted tetrazoles as is known, can exist in two isomeric forms, viz:

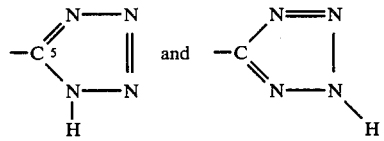

which co-exist in a dynamic tautomeric, equilibrium mixture.

A variety of methods are described in the literature for the synthesis of tetrazoles: Benson, Chem. Rev. 41, 1–61 (1947) and "Heterocyclic Compounds," Vol. 8, edited by Elderfield, John Wiley & Sons, Inc., N.Y. (1967). The preparation of 5-substituted tetrazoles by the reaction of an alkyl or aryl nitrile with hydrazoic acid is described in the above references, by Buckler et al., J. Med. Chem. 13, 725–9 (1970) and by Juby et al., J. Med. Chem. 11, 111–7 (1968). The literature methods employ rather strenuous reaction conditions such as elevated temperatures and prolonged reaction times which, if applied to the 6-amino 6-(N-protected amino)-2,2-dimethyl-3-cyanopenams of this invention, would result in considerable degradation of the reactants and products.

SUMMARY OF THE INVENTION

This invention comprises a process for the conversion, under relatively and surprisingly mild conditions, of 6-amino-2,2-dimethyl-3-cyanopenams to corresponding 6-amino- and 6-(N-protected-amino)-2,2-dimethyl-3-(5-tetrazolyl) penams by reaction with azide ion in the presence of an acid. The process is illustrated by the following equation:

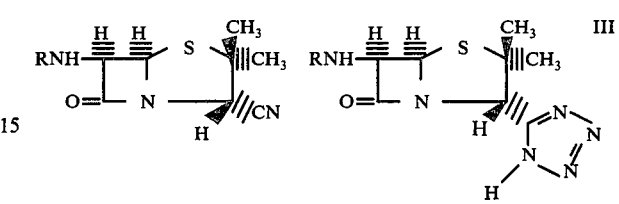

wherein R is as defined above.

Compounds of formula III wherein R is hydrogen readily form acid addition salts with organic and inorganic acids. Such compounds as well as the parent compound are included within the scope of this invention.

DETAILED DESCRIPTION OF THE INVENTION

In general the process of this invention comprises reacting an appropriate 6-amino or 6-(N-protected-amino)-2,2-dimethyl-3-cyanopenam of formula III with a source of azide ion in a reaction-inert solvent.

The present process is broadly applicable to a great variety of precursors to compounds of formula I as is evident from Reaction Scheme I.

REACTION SCHEME I[a]

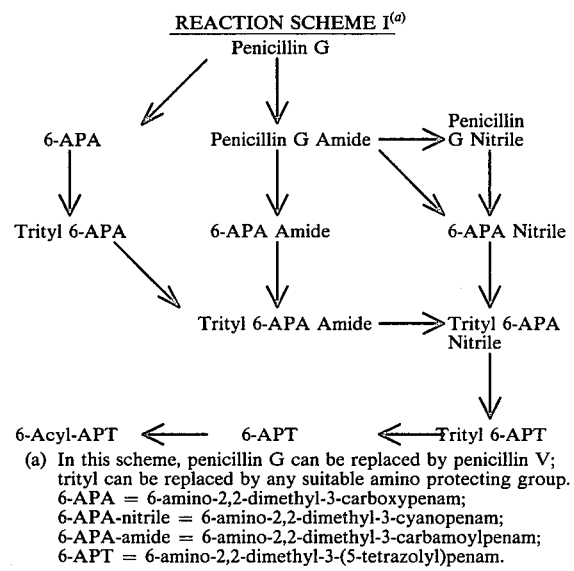

(a) In this scheme, penicillin G can be replaced by penicillin V; trityl can be replaced by any suitable amino protecting group.
6-APA = 6-amino-2,2-dimethyl-3-carboxypenam;
6-APA-nitrile = 6-amino-2,2-dimethyl-3-cyanopenam;
6-APA-amide = 6-amino-2,2-dimethyl-3-carbamoylpenam;
6-APT = 6-amino-2,2-dimethyl-3-(5-tetrazolyl)penam.

The azide ion can be derived from a variety of sources. The only criterion appears to be that the particular source chosen be capable of releasing azide ion under the conditions; i.e., solvent, temperature, of a given reaction. Suitable sources of azide ions are inorganic and organic azides. In the case of organic azides, the organic moiety must be strongly electron withdrawing in nature. Representative sources of azide ions are metal azides, especially alkali metal azides, trialkylsilyl azides having from one to four carbon atoms in each of the alkyl groups, such as trimethylsilyl azide and triethylsilyl azide, tetra-n-butylammonium azide, tetramethylguanidinium azide, hydrazoic acid, ammonium azide, trifluoromethylazide, N,N-dimethylanilinium azide, N-methyl-morpholinium azide and triethylammonium azide.

The molar ratio of azide to cyanopenam reactant is generally held in the range of from about 1:1 to about 6:1 to minimize destruction of the penam ring system. Higher ratios can be used but are generally accompanied by reduced yields of the desired tetrazole product.

The presence of a source of acid as catalyst during the reaction is desirable. In some cases, as when using a metal azide as source of azide ion, an acid source is necessary for reaction to take place. Lewis acids such as boron trifluoride also function as catalysts in reactions involving hydrazoic acid and metal azides, e.g. sodium azide.

A great variety of acid sources such as organic and inorganic acids can be used as catalyst in the process when a metal azide is used. The principle requirement is that the acid be sufficiently soluble in the solvent system used to permit reaction to occur. This aspect is, of course, readily determined by simple experiment. Representative acids are alkane sulfonic acids such as methane and ethane sulfonic acids, p-toluenesulfonic acid, benzenesulfonic acid, naphthalenesulfonic acids, alkanoic acids such as acetic, n-butyric, octanoic, benzoic and substituted benzoic acids, hydrogen chloride, hydrogen bromide and cation exchange resins.

Amine acid addition salts, especially amine hydrochlorides, appear to be equivalent to acids such as those enumerated above in this process and can be used in place of such acids. The acid addition salts of a great variety of amines, including primary, secondary and tertiary amines, can be used. The nature of the acid portion of the acid addition salt is immaterial to the operability of this process. However, certain acid addition salts are favored over others for such reasons as availability, ease of preparation and solubility in the reaction mixture. The suitability of a given amine acid addition salt is easily determined by carrying out the process of this invention using the amine acid addition salt as source of acid.

Non-nucleophilic amines are favored since they do not enter into sidereactions with the β-lactam of the nitrile reactant. Favored acid addition salts are the salts with mineral acids and other acids enumerated above under acid sources. The preferred amine acid addition salts are the hydrochloride salts of non-nucleophilic tertiary amines such as triethylamine, tri-n-propylamine, tri-n-butylamine, trimethylamine, N,N-dimethylaniline, N-methylpiperidine and N-methylmorpholine because of the satisfactory conversions of nitrile to tetrazole they afford in this process.

Suitable reaction-inert solvents for this process are halogenated hydrocarbons such as trichloroethanes, chloroform, and methylene chloride, ethers such as dioxane, tetrahydrofuran, dimethyl, and diethyl ethers of ethyleneglycol and diethylene glycol, macrocyclic polyethers (crown compounds,) benzene, xylene tetralin and pyridine. Chloroform is a favored solvent in view of the favorable yields it affords and the ease of recovery of the tetrazolylpenams therefrom.

It is advantageous, but not necessary, to use anhydrous solvents in order to avoid detrimental effects on the yields of the desired tetrazole derivatives. Up to 5% by volume of water appears to be permissible.

In order to expedite the reaction the solvent should desirably be one which completely dissolves all reactants. As one skilled in the art appreciates, complete solubility is, however, not necessary. Partial solubility of reactants in the solvent system is sufficient to permit reaction to occur at an acceptable rate.

The reaction is generally conducted over the range of from about 20° C. to about 110° C. The favored temperature range is from about 25° C. to about 80° C. and the preferred range from about 40° C. to about 70° C. Temperature is not a critical factor and lower or higher temperatures can be employed. Lower temperatures, of course, require longer reaction times than do the higher temperatures. Temperatures above about 110° C. are usually avoided to minimize decomposition of reactants and products.

The reaction period depends in part upon the reactants and the solvent system used. As a general rule, the reaction is completed in periods ranging from about 1.5 to about 24 hours.

The molar ratio of catalysts or amine acid addition salt catalysts to azide source generally varies from about 1:1 to about 5:1. Higher ratios are usually avoided in order to minimize degradation of the penam ring system. In a strict sense the acid or amine salt is hardly a catalyst. It is, however, convenient to refer to it is such.

The yield of tetrazole product is improved by the presence of a base in the reaction mixture, which suppresses attack of azide on the β-lactam of the cyanopenam. The nature of the base can vary widely. It should desirably be soluble in the reaction mixture and non-nucleophilic. The favored bases are organic amines, primary, secondary, or tertiary. When an amine acid addition salt is used as catalyst, it is convenient to use an excess of the corresponding amine as the base. The amount of base when used in generally not greater than 3 moles per mole of azide since greater amounts appear to cause degradation of the penam ring system. Preferred bases are triethylamine, piperidine, N,N-dimethylaniline, aniline, N-methylpiperidine and N-methylmorpholine.

The 3-(5-tetrazolyl)penam compounds of formula I are recovered by such procedures as concentration of the reaction mixture under reduced pressure, and chromatography of the crude reaction product on silica gel using chloroform 10% methanol as eluent followed by evaporation of the eluate, and recrystallization from a suitable solvent system.

A favored recovery procedure, especially when using chloroform as solvent, comprises washing the reaction mixture successively with aqueous acid and water followed by drying and concentrating the chloroform solution. The product separates and is isolated by filtration or centrifugation.

In other modifications of Reaction Scheme I, 6-amino-2,2-dimethyl-3-cyanopenam, and the nitriles of penicillin G and penicillin V can be used in this process according to the procedures described herein to produce the corresponding tetrazole surrogates.

The 3-cyanopenams of formula III are conveniently prepared by dehydration of the corresponding 3-carbamyl penams of formula IV

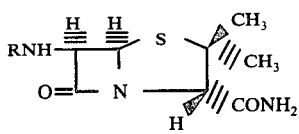

wherein R is as defined above. Suitable dehydrating agents are acetic anhydride, pyridine, and an arylsulphonyl chloride (e.g., p-toluenesulphonyl chloride) or methanesulphonyl chloride, ethanesulphonyl chloride, phosphorous pentachloride and phosphorous oxychloride together with a base such as pyridine, mixtures of thionyl chloride and N,N-dimethylformamide, and phosgene in the presence of pyridine. The preferred dehydrating procedure comprises treating the appropriate compound of formula IV with p-toluenesulphonyl chloride in pyridine at about 65°-70° C. for periods of about 30 to 60 minutes.

Alternatively, they are conveniently prepared by deacylation of 6-(2-phenylacetamido)-2,2-dimethyl-3-cyanopenam or 6-(2-phenoxyacetamido)-2,2-dimethyl-3-cyanopenam by chemical methods. Chemical deacylation is conveniently accomplished by the procedure of U.S. Pat. No. 3,499,909. This procedure comprises reacting one of said 6-(acylamido)-2,2-dimethyl-3-cyanopenams in a reactioninert solvent under anhydrous conditions at a temperature below about 25° C. with a suitable halogenating agent in the presence of an acid binding agent to form an imino halide. Representative solvents are chloroform, methylene chloride, 1,2-dichloroethane, tetrahydrofuran, dimethyl ether of ethylene glycol, nitromethane, diethylether, isopropylether, etc. Suitable halogenating agents are phosphorous pentachloride, phosphorous pentabromide, phosphorous trichloride, phosphorous tribromide, phosphorous oxychloride, phosgene, p-toluenesulfonyl chloride, oxalyl chloride, etc. Representative acid binding amines are tertiary amines such as dimethylaniline, quinoline, lutidine, pyridine.

The imino chloride, the preferred form of imino halide, is converted to a corresponding imino ether by treatment with a primary alcohol at a temperature below about 25° C., desirably at a temperature between about −20° C. and about −60° C, and preferably at about −40° C., under anhydrous conditions. Suitable alcohols are alkanols of from 1 to 12 carbon atoms, and preferably of from 1 to 4 carbon atoms, phenylalkanols having from 1 to 7 carbon atoms in the alkanol moiety; alkanediols having from 2 to 6 carbon atoms; alkoxyalkanols having from 2 to 6 carbon atoms; and others such as are enumerated in U.S. Pat. No. 3,499,909. Representative alcohols are methanol, ethanol, propanol, n-butanol, amyl alcohol, decanol, benzyl alcohol β-phenylethanol, 3-phenyl-1-propanol, 1,3-propanediol, 1,6-hexanediol, 1,2-methoxyethanol, 2-butoxyethanol. The preferred alcohols are methanol, ethanol, propanol, and butanol. The imino ether is then cleaved by mild hydrolysis or alcoholysis under acid conditions.

In a further and surprising modification, 6-(2-phenylacetamido)- or 6-(2-phenoxyacetamido)-2,2-dimethyl-3-carbamylpenams are directly converted to 6-amino-2,2-dimethyl-3-cyanopenam by a "one-pot" process using the procedure described above but using at least about two molar equivalents of halogenating agent per mole of 6-(2-phenylacetamido)- or 6-(2-phenoxyacetamido)-2,2-dimethyl-3-carbamyl)penam.

The amide precursors (see Scheme I) are prepared according to the procedure of U.S. Pat. No. 2,593,852 which comprises reacting the appropriate 6-amino-2,2-dimethyl-3-carboxypenam anhydride (e.g., an anhydride of penicillin G, penicillin V) with ammonia in a solvent such as isopropanol. 6-Triphenyl-methylamino-2,2-dimethyl-3-carbamylpenam is described by Koe, Nature, 195, 1200–1 (1962). Alternatively, they are prepared according to the procedure described by Johnson, J. Am. Chem. Soc. 75, 3637-7 (1953) which comprises reacting the triethylammonium salt of the appropriate 6-amino-2,2-dimethyl-3-carboxypenam compound with ethyl chloroformate in a reaction-inert solvent such as chloroform or methylene chloride to form a mixed anhydride. Reaction of the mixed anhydride with ammonium hydroxide affords the amide. A variety of ammonium salts can be used in place of the triethylammonium salt. A favored salt is the N-methylmorpholinium salt of the 6-amino-2,2-dimethyl-3-carboxypenam reactant because of the satisfactory yields it affords.

The compounds of formula III wherein R is an amino-protecting group (other than 2-phenylacetyl or 2-phenoxyacetyl) are readily prepared by alkylation of 6-amino-2,2-dimethyl-3-cyanopenam with the appropriate halide derivative RX (X=Cl, Br, I) of the amino-protecting group. The procedure comprises reacting 6-amino-2,2-dimethyl-3-cyanopenam in chloroform or methylene chloride solution with the appropriate RCl and RBr and an equivalent amount of an acid acceptor. The reaction is initially conducted at about 0°-5° C. for 0.5 to 2.0 hours and then at ambient temperature for up to 72 hours. The product, if desired, is isolated by standard procedures (e.g., evaporation of solvent).

When R of formula III is 2,2,2-trichloro (or tribromo)ethoxycarbonyl the compounds are prepared by reaction of 6-amino-2,2-dimethyl-3-cyanopenam with 2,2,2-trichloro (or tribromo)ethylchloroformate in a reaction-inert solvent such as dioxane, at about −20° to +25° C. in a Schotten-Baumann reaction.

The triphenylmethyl protecting group and substituted derivatives thereof of formula II are removed by treating the protected compound with a wide variety of acidic reagents and conditions known in the art for removal of a triphenylmethyl group are operable in this process. For example, it is possible to use a sulfonic acid, such as methanesulfonic acid, benzenesulfonic acid or p-toluenesulfonic acid; and anhydrous hydrohalic acid, such as hydrogen chloride or hydrogen bromide; or an alkanoic acid such as acetic acid, propionic acid, chloroacetic acid, trifluoroacetic acid and the like. The reaction is normally carried out by dissolving the starting material in an appropriate solvent and adding about two molar equivalents of the acid reagent at or about ambient temperature. Reaction is complete within about one hour, and the product is present in the reaction medium in the form of the acid-addition salt corresponding to the acidic reagent used. A solvent should be chosen which will dissolve the starting penam, and examples of solvents which find use are: ethers, such as diethyl ether, tetrahydrofuran, dioxane and 1,2-dimethoxyethane; chlorinated hydrocarbons, such as chloroform, methylene chloride and 1,2-dichloroethane; lower aliphatic ketones, such as acetone, methyl ethyl ketone and methyl isobutyl ketone; esters, such as ethyl acetate and butyl acetate; hydrocarbons, such as hexane, cyclohexane and benzene; and lower alkanols, such as methanol, ethanol and butanol. Although it is common to use about two molar equivalents of acid in this process, only one molar equivalent is necessary when the reaction is carried out in the presence of one molar equivalent of water, or the acid is introduced as a monohydrate. However, as will be realized by one skilled in the art, the product from this reaction should not be exposed to an excess of acid for prolonged periods, since in this case there is a danger of destroying the $\beta$-lactam system. A particularly convenient mode of operation for this process, is to choose an acid-solvent system such that the starting material is soluble, but the acid addition salt generated during the reaction precipitates as it is formed. It can then be recovered by filtration at the end of the reaction. When using the combination of p-toluenesulfonic acid in acetone, the p-toluenesulfonate salt of the product often precipitates.

When the amino-protecting group is a 2,2,2-trihaloethoxycarbonyl group it is removed from the compound of formula I by a reductive deblocking step. This comprises treating the protected compound with zinc dust in 90% aqueous formic acid or a zinc-copper couple in formic acid diluted with acetonitrile in the manner described by Chauvette et al., J. Org. Chem. 36, 1259-67 (1971).

6-amino-2,2-dimethyl-3-(5-tetrazolyl)penam is, as noted above, a valuable intermediate for the preparation of 6-acylamido-2,2-dimethyl-3-(5-tetrazolyl)penams, antibacterial agents of significant activity. Such compounds are prepared by acylation of 6-amino-2,2-dimethyl-3-(5-tetrazolyl)penam (6-APT) with an activated derivative of the appropriate carboxylic acid, in an appropriate solvent system. An activated derivative commonly used is an acid halide, such as an acid chloride. In a typical acylation procedure, approximately one molar equivalent of an acid chloride is added to a solution of 6-APT, or a salt thereof, dissolved in a solvent such as chlorinated hydrocarbon, for example, chloroform or methylene chloride; an ether, for example, tetrahydrofuran or 1,2-dimethoxyethane; an ester, for example, ethyl acetate or butyl acetate; a lower aliphatic ketone, for example, acetone or methyl ethyl ketone or a tertiary amide, for example, N,N-dimethylformamide or N-methylpyrrolidone; at a temperature in the ranges from about $-40°$ C. to about 30° C., and preferably from about $-10°$ C. to about 10° C., optionally in the presence of about one molar equivalent of an acid-binder, e.g., triethylamine, pyridine or sodium bicarbonate. The reaction is complete within a short period, i.e., approximately one hour, and the product is isolated by techniques well known in the art, having full regard for the sensitive nature of the $\beta$-lactam moiety of the product. For example, the reaction mixture is evaporated to dryness and a water-immiscible organic solvent and water are added. In those cases where the product precipitates, it is filtered off. If the product does not precipitate, then the pH of the aqueous phase is adjusted to an appropriate value and the phase containing the product is evaporated. The crude product thus obtained can be purified further if desired. An alternate procedure useful for acylation with acid halides involves the use of an aqueous solvent system. In this procedure, which approximates the Schotten-Baumann procedure, the acid halide is added to a solution of the starting material in water, or a mixture of water and another inert solvent being maintained with the range from about 6.0 to about 9.0 before, during, and after the addition. At the end of the reaction, the product can often by induced to precipitate by adjustment of the pH. Alternatively, it can be extracted into a water-immiscible solvent, which is then evaporated to dryness.

Another activated derivative of the carboxylic acid useful as an acylating agent is a mixed anhydride. In this procedure a solution of the preformed mixed anhydride is reacted with 6-APT, usually as a tertiary amine salt, for example the triethylamine salt at a temperature in the range from about $-30°$ C. to about 20° C., and preferably at about $-10°$ C. In most instances the mixed anhydride and the 6-APT are contacted substantially in a 1:1 molar ratio. The product is usually isolated by evaporating the reaction mixture to dryness, and then adding a water-immiscible organic solvent and water. By careful adjustment of the pH, the product sometimes precipitates. In other cases the phases are separated, and the product-containing phase is evaporated to dryness. The crude product so obtained can be purified further if desired.

Another variation comprises conversion of the carboxylic acid to an active ester, followed by treatment with 6-APT or a salt thereof. Active esters which can be used are, for example, phenyl esters, such as p-nitrophenyl and 2,4,5-trichlorophenyl esters, thiol esters, such as thiolphenyl and thiolmethyl esters; and N-hydroxy esters, such as N-hydroxysuccinimide and N-hydroxyphthalimide esters. The esters are prepared by methods well established in the art, and the acylation is conveniently conducted by dissolving the active ester and the 6-APT or a salt thereof in a dipolar aprotic solvent such as N,N-dimethylformamide, N,N-dimethylacetamide or N-methylpyrrolidone. The solution is stored at about ambient temperature for several hours, for example overnight, and then the product is isolated by standard methods. In some instances the product can be isolated very simply by causing it to precipitate by the addition of a nonsolvent, such as diethyl ether or acetone, It is then filtered off, and it can be purified, if desired, further. In many cases the active ester used in this process can be replaced by the corresponding acid azide.

A still further variation comprises contacting 6-APT with a carboxylic acid in the presence of certain agents known in the art for forming peptide bonds. Such agents include carbodiimides, for example, dicyclohexylcarbodiimide and 1-ethyl-3-(3-dimethylaminopropyl)-carbodiimide, alkoxyacetylenes, for example, methoxyacetylene and ethoxyacetylene, and N-ethoxycarbonyl-2-ethoxy-1,2-dihydroquinoline. The reaction is carried out in an appropriate solvent, i.e. one which will serve to dissolve the reactants, and does not adversely interact with the starting materials or the product, for example acetonitrile, N,N-dimethylformamide and N-methypyrrolidone.

Implicit in the acylation methods described above, is the observation that in a process for the acylation of 6-APT, hydrogen substituents located on the 6-amino group and tetrazolyl moiety can successfully be replaced by trialkylsilyl substituents. Said trialkylsilyl substituents are then removed, and replaced by hydrogen, at the end of the acylation, simply by brief exposure of the product to a protic solvent system, such as water or a lower-alkanol, for example, methanol or ethanol. By virtue of the ready availability of the starting materials, the trimethylsilyl group is a preferred member. It can be introduced into the starting 6-APT by methods well known in the art, such as, for example, using trimethylchlorosilane or N-trimethylsilylacetamide, as discussed by Birkofer and Ritter in *Angewandte*

*Chemie* (International Edition in English) 4, 417–418 and 426 (1965). Conditions must be chosen, however, which are compatible with the β-lactam group of the penam nucleus.

In addition to the step-wise reactions in Reaction Scheme I, it is pososible, and frequently advantageous, to conduct various of the steps in a "one-pot" process without isolation of the intermediates in Scheme I. For example, 6-APA-nitrile can be converted in a "one-pot" process of trityl 6-APT. The trityl 6-APT can, in turn, be detritylated and acylated in a "one-pot" process to produce a 6-acyl-APT. Further, penicillin G amide and can be deacylated and dehydrated in a single reaction to produce 6-APA nitrile. These "one-pot" processes eliminate the need to isolate and/or purify intermediates, are more convenient, simple, and economical to run, and frequently afford improved yields over those realized by proceeding in step-wise fashion.

The 6-acylamido-2,2-dimethyl-3-(5-tetrazolyl)penams, for which the products described herein serve as intermediates are valuable antibacterial agents as previously noted. They are active in vitro and in vivo against a wide variety of gram-positive and gram-negative bacteria. Their useful activity can readily be demonstrated by in vitro tests against various organisms in a brain-heart infusion medium by the usual two-fold serial dilution technique. Their in vitro activity renders them useful for topical application in the form of ointments, creams and the like, or for sterilization purposes, e.g. sick-room utensils.

They are also effective antibacterial agents in vivo in animals, including man, not only via the parenteral route of administration but also by the oral route of administration.

The oral and parenteral dosage levels for the herein described compounds are, in general, on the order of up to 200 mg./kg. and 100 mg./kg. of the body weight per day, respectively.

For such purposes, the pure materials or mixtures thereof with other antibiotics can be employed. They may be administered alone or in combination with a pharmaceutical practice. For example, they may be administered orally in the form of tablets containing such excipients as starch, milk sugar, certain types of clay, etc., or in capsules alone or in admixture with the same or equivalent excipients. They may also be administered orally in the form of elixirs or oral suspensions which may contain flavoring or coloring agents, or be injected parenterally, that is, intramuscularly or subcutaneously. For parenteral administration, they are best used in the form of a sterile aqueous solution which may be either aqueous such as water, isotonic saline, isotonic dextrose, Ringer's solution or non-aqueous such as fatty oils of vegetable origin (cotton seed, peanut oil, corn, sesame) and other non-aqueous vehicles which will not interfere with the therapeutic efficiency of the preparation and are non-toxic in the volume or proportion used (glycerol, propylene glycol, sorbitol). Additionally, compositions suitable for extemproaneous preparation of solutions prior to administration may advantageously be made. Such compositions may include liquid diluents, for example, propylene glycol diethyl carbonate, glycerol, sorbitol, etc.; buffering agents, as well as local anesthetics and inorganic salts to afford desirable pharmacological properties.

EXAMPLE 1

6-Triphenylmethylamino-2,2-Dimethyl-3-Cyanopenam

A. Triethylamine salt of 6-triphenylmethylamino-2,2-dimethylpenam-3-carboxylic acid.

Tritylchloride (61.2g., 0.22 mole) is added to a mixture of 6-aminopenicillanic acid (43.3g., 0.20 mole) and triethylamine (5.56 ml.) in chloroform (300 ml.) at about 5° C. The somewhat exothermic reaction is stirred and allowed to rise gradually to room temperature. It is stirred at room temperature for three days. Evaporation of the reaction mixture affords the title product which is used without purification.

B. 6-Triphenylmethylamino-2,2-dimethyl-3-(carbamyl)penam.

Ethyl chloroformate (35.8g., 0.33 mole) is added to an acetone (300 ml.) solution containing 0.3 mole (137.3 g.) of the salt prepared in Procedure A above and cooled in an ice-bath to about 0° C. The temperature rises to about 10° C. and a precipitate of triethylamine hydrochloride forms. The temperature soon falls to about 0° C. and stirring of the reaction mixture is continued for 45 minutes. It is then filtered and the precipitate washed with acetone (10–20 ml.) The combined filtrate and washings are placed in a 5 liter round-bottom flask containing a solution of diammonium phosphate (311.4 g.) in water (1750 ml.) The mixture is stirred at room temperature for 35 minutes and then extracted with chloroform (2 × 800 ml.). The combined chloroform extracts are washed successively with ice-cold 0.1 N hydrochloric acid (1.5), 5% sodium bicarbonate solution (2 × 1.5 l.), water (1.1) and saturated sodium chloride solution (750 ml.) and then dried ($Na_2SO_4$).

The chloroform solution is concentrated under reduced pressure at room temperature to a light orange viscous oil. The oil is taken up in benzene (350 ml.) and the resulting solution added dropwise with stirring to hexane (3000 ml.). The white precipitate which forms is filtered, washed with hexane and dried in vacuo. Yield: 138 g. (100.5%) of crude amide.

It is purified by column chromatography on silica gel as follows. Crude product (55 g.), dissolved in chloroform (100 ml.) is run down a silica gel (70–230 mesh) column (85 mm. × 350 mm.) and the column eluted with chloroform. The eluate is evaporated to dryness to give the pure product (40 g.).

C. Dehydration of 6-triphenylmethylamino-2,2-dimethyl-3-(carbamyl)penam.

The 3-carbamyl derivative from Preparation B above (10.4 g., 0.0227 mole) is dissolved in pyridine (45 ml.) and methanesulfonyl chloride (2.7 ml.) added dropwise over a five minute period. The reaction mixture is stirred for two days and then concentrated to dryness in vacuo. The residue is taken up in chloroform (200 ml.) and the solution washed with a saturated aqueous solution of copper sulfate (2 × 250 ml.). It is dried ($Na_2SO_4$) and evaporated to dryness. The oily residue is purified by dissolution in chloroform (200 ml.) and the solution washed with a saturated aqueous solution of copper sulfate (2 × 250 ml.). It is dried ($Na_2SO_4$) and evaporated to dryness. The oily residue is purified by dissolution in chloroform and chromatography on a silica gel (70–230 mesh; 50 mm. × 450 mm.) column using chloroform as eluant. Evaporation of the eluate gives the product 6-triphenylmethylamino-2,2-dimethyl-3-cyanopenam.

Trituration of the product in benzene produces a benzene solvate; m.p. 103°–112° C.

The NMR spectrum (in DMSO-$D_6$) shows absorption bands at 1.49 + 1.57 (s, 3H each, C-2 methyls) 3.15 (d, J=ca. 11 $H_z$, 1H, NH), 4.20–2.27 (m, 2H, $H_5$ + $H_6$), 4.55 (s, 1H, $H_3$), and 7.10–7.80 (m, 15H, aromatic protons)ppm.

EXAMPLE 2

6-Amino-2,2-Dimethyl-3-Cyanopenam Tosylate

A mixture of 6-triphenylmethylamino-2,2-dimethyl-3-cyanopenam (2.2g. 5 mmoles), p-toluenesulfonic acid monohydrate (681 mg., 5 mmoles) and anhydrous acetone (20 ml.) is stirred at room temperature for one hour. A thick white precipitate formed after a half-hour of stirring and anhydrous acetone (20 ml.) is added to facilitate stirring. The solid is filtered, washed first with acetone and next with ether and then air dried. M.P. 171°–172° C.

The NMR spectrum (in DMSO-$D_6$) shows absorption bands at 1.52 + 1.65 (s, 3H each, C-2 methyls), 2.30 (s, 3H, tosyl-$CH_3$), 5.10 + 5.54 (d, 1H each, J=5.0 $H_z$, $H_5$ + $H_6$), 5.47 (s, 1H, $H_3$), 7.15 + 7.47 (2d, J=8.0$H_z$, 4H tosyl aromatic protons), and 8.03 (s, 3H, $NH_3$) ppm.

Repetition of the above process but using the following acids in place of p-toluenesulfonic acid monohydrate affords 6-amino-2,2-dimethyl-3-cyanopenam. HA wherein HA corresponds to the acid used:
 benzene sulfonic acid
 methane sulfonic acid
 hydrogen chloride
 hydrogen bromide
 acetic acid
 trifluoroacetic acid
 chloroacetic acid.

EXAMPLE 3

6-Amino-2,2-Dimethyl-3-Cyanopenam Hydrochloride (from 6-(2-phenylacetamido)-2,2-dimethyl-3-cyanopenam, Penicillin G Nitrile)

To a suspension of phosphorous pentachloride (520 mg., 2.5 mmoles), quinoline (645 mg., 5 mmoles) and chloroform (8ml.) at −5° C. is added 6-(2-phenylacetamido)-2,2-dimethyl-3-cyanopenam (730 mg., 2 mmoles). The mixture is stirred at −5° C. for 1 hour and is then treated with n-propanol (1.12 g.). Stirring is continued for a half hour at −5° C. after which the mixture is removed from the cooling bath and allowed to warm to room temperature. It is then diluted with a solution of acetone-isopropyl ether (15 ml. of 25–75 solution) and the precipitate which forms separated by filtration and washed with acetone-isopropyl ether (30 ml. of 25–75 solution). It is then triturated in chloroform (25 ml.), filtered and dried on a porous plate. The product is an off-white waxy solid (783 mg., 77%). (m.p. 140°–200° (slow decomposition).

The NMR spectrum (in DMSO-$D_6$) shows absorption bands at 1.58 + 1.68 (s, 3H each C-2 methyls), 5.10 + 5.60 (d, J=4.0 $H_z$, 2H, $H_5$ + $H_6$), 5.50 (s, 1H, $H_3$) and ca. 7.30 (broad s, 3H, $NH_3$) ppm.

Repetition of this procedure but using phosphorous tribromide in place of phosphorous pentachloride and methanol, ethanol or n-butanol in place of n-propanol affords the same product.

EXAMPLE 4

6-Amino-2,2-Dimethyl-3-Cyanopenam Hydrochloride (From penicillin G amide)

Penicillin G amide trihydrate (20g., 0.0516 mole) is dissolved in chloroform (300 ml.) and the solution dried with anhydrous sodium sulfate. The solution is then evaporated to dryness in vacuo and the residue azeotropically dried by addition and distillation of benzene (30 ml.) The azeotropic drying is repeated.

The dry residue is dissolved in chloroform (300 ml.) and quinoline (33.32g., 0.258 mole) added. The mixture is cooled to −5° C. and a suspension of $PCl_5$ (24.13g., 0.116 mole, 2.25 equivalents) in chloroform (75 ml.) added in portions over a twenty minute period. The resulting suspension is stirred at −5° C. for 1 hour, and then at +5° C. for 1 hour. It is then warmed to room temperature and stirred for an additional 45 minutes. The reaction mixture is cooled to −3° C. and n-propanol (37.22 ml.) added. The temperature rises to about 4° C. The cooling bath is removed and the mixture allowed to warm to 13° C. Saturated aqueous sodium chloride (3 ml.) is added and the mixture chilled and stirred vigorously. The white solid which forms is filtered off, washed with methylene chloride and air-dried. (4.72g., 37.5%).

The NMR spectrum (in DMSO-$D_6$) shows absorption bands of this compound is identical to those of Example 3.

Repetition of this procedure but using methanol, ethanol or n-butanol in place of n-propanol provides the same product.

EXAMPLE 3

6-Amino-2,2-Dimethyl-3-Cyanopenam Hydrochloride (from Penicillin G Amide)

Phosphorous pentachloride (45.7g., 0.22 mole) is added over a three minute period to a mixture of quinoline (64.5g., 0.5 mole) in dry chloroform (500 ml.) chilled to 10° C. The resulting mixture is cooled to −10° C. and then penicillin G amide (33.4g., 0.1 mole) added over a ten minute period while maintaining the temperature at −5° to −10° C. The mixture is stirred for 1 hour and then chilled to −50° C. (dry ice-acetone). Dry 1-propanol (66g., 1.1 moles) is then added dropwise to the mixture over a ten minute period while holding the temperature below −40° C. The cooling bath is removed and the temperature allowed to rise to −30° C. After 30 minutes at −30° C., the reaction mixture is warmed to −5° C. Saturated aqueous sodium chloride solution (10 ml.) is added, the temperature brought to, and held, at +5° C. for 30 minutes.

The product crystallizes and is collected by filtration, washed with chloroform and dried in vacuo. Yield = 16.2 g. (70%). M.P. = 200° C. (dec.)

The NMR spectrum (in DMSO-$D_6$) shows absorption bands of this compound is identical to those of Example 3.

Repetition of this procedure but using penicillin V amide in place of penicillin G amide produces the same product.

EXAMPLE 6

6-Amino-2,2-Dimethyl-3-Cyanopenam Hydrochloride

A solution of anhydrous penicillin G amide (33.3g., 0.10 mole) in dry ethanol free chloroform (343 ml.) at −5° C. is added with cooling and stirring to a cold (−5° C.) slurry of phosphorous pentachloride (48.2g., 0.232 mole) in chloroform (170 ml.) containing quinoline (68.99g., 0.535 mole) over a 15 minute period. The reddish-orange mixture is stirred for 45 minutes at about −1° C. It is then chilled to −30° to −35° C. and absolute ethanol (85.5 ml.) added. The temperature is held to −30° C. to −35° C. during the rapid, about 3 minutes, addition of the alcohol. The cooling bath is removed and the reaction mixture allowed to warm to about −5° C. at which point brine (8.55 ml.) is rapidly added with stirring. The mixture is stirred continuously while allowing the temperature to rise. The white precipitate which forms is filtered, washed with chloroform and then ether and dried. Yield of crude title product = 18.39g. The principal contaminant is sodium chloride.

On the basis of quantitative analysis of the crude product, 18.4% by weight of sodium chloride is present in the crude. The yield of title product, corrected for the salt content, is then 64.2%. It can be used as is in subsequent reactions or, if desired, purified.

Purification is achieved by converting the hydrochloride salt to the free base as is described in Example 8.

The NMR spectrum (in DMSO-$D_6$) shows absorption bands of this compound identical to those of Example 3.

EXAMPLE 7

6-Triphenylmethylamino-2,2-Dimethyl-3-Cyanopenam

Triethylamine (44.5g., 0.44 mole) is added to a slurry of 6-amino-2,2-dimethyl-3-cyanopenam hydrochloride (46.6g., 0.2 mole) in methylene chloride (1500 ml.) at room temperature and the resulting mixture stirred for 20 minutes. Triphenylmethyl chloride (66.9 g., 0.24 mole) is added in one portion to the mixture which is stirred at room temperature for 3.5 hours. The methylene chloride layer is separated and washed with water (5 × 100 ml.). It is then dried ($Na_2SO_4$) and concentrated in vacuo to orange-red viscous oil. Methanol (50 ml.) is added and the mixture stirred for a half hour to give a yellow-white solid. The solid is filtered, resuspended in fresh methanol, and the suspension stirred for a half hour. The solid is recovered by filtration and dried in a vacuum over at room temperature. Yield of crude = 47 gms. M.p. 116°–119° C.

It is purified as follows:

The crude nitrile (53 g.) is dissolved in isopropanol (424 ml.) and allowed to stand at room temperature. The crystalline solid which separates is filtered and dried in a vacuum over at room temperature (18 g.). Additional solid which separates from the filtrate on standing is redissolved by heating the filtrate. The hot filtrate is filtered to remove a small amount of insolubles and allowed to stand to yield a second crop of crystals which is filtered and dried as was the first crop (9.13 g.) Total yield 27.13 g. M.P. 160°–163° C.

The NMR spectrum (in $CDCl_3$) shows absorption bands at 1.40 + 1.57 (*s*, 3H each, C-2 methyls), 3.15 (*d*, J=*ca*. 11.0 $H_z$, 1H, NH), 4.20–4.72 (*m*, 2H, $H_5$ + $H_6$), 4.55 (*s*, 1H, $H_3$); and 7.10–7.82 (*m*, 15H aromatics)ppm.

EXAMPLE 8

6-Amino-2,2-Dimethyl-3-Cyanopenam

Triethylamine (666 mg., 6.6 mmoles) is added to a suspension of 6-amino-2,2-dimethyl-3-cyanopenam hydrochloride (1.3g, 6.0 mmoles) in methylene chloride (100 ml.) and the mixture stirred at room temperature for 20 minutes.

The cloudy mixture is then concentrated in vacuo to a solid. Ether (100 ml.) is added to the solid residue which is thoroughly stirred and then filtered to remove triethylamine hydrochloride. The filter cake is washed with ether (25 ml.) and the combined ether solutions concentrated in vacuo to a white solid. The solid is slurried in hexane (50 ml.), filtered and air-dried. Yield 750 mg. (64%); m.p. 80°–84° C.

The NMR spectrum (in $CDCl_3$) shows absorption bands at 1.60 + 1.75 (*s*, 3H each, C-2 methyls), 1.89 (*s*, 2H, $NH_2$), 4.62 (*s*, 1H, $H_3$), 4.60 and 5.48 (*d*, J=4.0$H_z$, 2H, $H_5$ + $H_6$) ppm.

EXAMPLE 9

6-(Di-[2-methylphenyl]phenylmethylamino)-2,2-Dimethyl-3-Cyanopenam

Triethylamine (444 mg., 4.4 mmole) is added to a suspension of 6-amino-2,2-dimethyl-3-cyanopenam (468 mg., 2 mmole) in methylene chloride (20 ml.) and the resulting mixture cooled to −10° C. A solution of α,α-di(2-methylphenyl) benzyl chloride (614 mg., 2 mmole) in methylene chloride (12 ml.) is added over a ten minute period and the resulting yellow solution stirred for 1 hour at −10° C. The cooling bath is removed and the mixture stirred and allowed to warm to room temperature. It is stirred for two hours at room temperature and is then concentrated under reduced pressure to a brown sludge. The sludge is chromatographed on a silica gel column (70-23- mesh., 380 × 20 mm. column) using chloroform as eluent. Fractions (15 ml. each) are collected. Fractions 13–19 are combined and concentrated in vacuo to dryness to give 155 mg. of product as a foam.

The NMR spectrum (in $CDCl_3$) shows absorption bands at 1.55 + 1.68 (*s*, 3H each, C-2 methyls), 2.02 + 2.08 (*s*, 3H each AR-$CH_3$), 3.2 (*d*, J=10 $H_z$, 1H, NH), 4.58 (*s*, 1H, $H_3$), 4.20–4.80 (*m*, 2H, $H_5$ + $H_6$), and 7.00–7.88 (*m*, 13H aromatics) ppm.

EXAMPLE 10

6-(diphenyl-[2-bromophenyl]methylamino)-2,2-Dimethyl-3-Cyanopenam

The procedure of Example 19 is repeated but using α,α-diphenyl-2-bromobenzyl chloride as tritylating agent in place of α,α-di(2-methyl-phenyl) benzylchloride.

The product is obtained as a light yellow, tacky oil. Upon standing the oil crystallizes to a white solid which is slurried in hexane, filtered, washed with hexane and air dried. Yield = 250 mg. (24%). m.p. = 192°–195° C.

The NMR spectrum (in $CDCl_3$) shows absorption bands at 1.55 + 1.63 (*s*, 3H each, C-2 methyls), 3.57 (broad D, J=*ca*. 10 $H_z$, 1H, NH), 4.28–4.66 (*m*, 3H, $H_3$, $H_5$, + $H_6$) and 7.02–8.06 (*m*, 14H, aromatic) ppm.

EXAMPLE 11

6-(Diphenyl-[2-methylphenyl]methylamino)-2,2-Dimethyl-3-Cyanopenam

To a mixture of 6-amino-2,2-dimethyl-3-cyanopenam hydrochloride (9.06g. 0.039 mole) in ethanol free chloroform (100 ml.) at −15° C. is added triethylamine (11.2 ml., 0.08 mole) followed by diphenyl-2-methylphenyl-methylchloride (11.4 g., 0.039 mole). The mixture is stirred for two hours and then washed successively with water (2 × 50 ml.), dilute aqueous acid (HCl) of pH 3.0 (2 × 50 ml. and brine 1 × 50 ml.). It is then dried with magnesium sulfate and silica (5 g.) added. It is immediately filtered and the filtrate evaporated under reduced pressure to a foam. The foam is taken up in a minimum volume of acetonitrile. Upon standing crystals separate. The white crystals are separated by filtration, washed with hexane and dried. Yield = 10.49g; m.p. 169°–172° C.

The NMR spectrum (in $CDCl_3$) shows absorption bands at 1.57 + 1.67 (2s, 3H, $C_2$ methyls), 2.03 (s, 3H, AR-$CH_3$), 3.23 (d, J=12$H_z$, 1H, NH), 4.60 (m, 3H, $H_3$, $H_5$ + $H_6$) and 7.44 (m, 14H, aromatic protons) ppm.

Repetition of this procedure but using the appropriately substituted triphenylmethyl chloride reactant in place of diphenyl-2-methylphenylmethyl chloride affords the following compounds:

| $R_1$ | $R_2$ | $R_3$ | $R_1$ | $R_2$ | $R_3$ |
|---|---|---|---|---|---|
| 4-Cl | H | H | 4-Cl | 4-$OCH_3$ | H |
| 4-Br | H | H | 3-$OCH_3$ | 3-$OCH_3$ | H |
| 4-F | H | H | 4-$OCH_3$ | 4-$OCH_3$ | H |
| 3-$OCH_3$ | H | H | 3-$CH_3$ | 3-$CH_3$ | 3-$CH_3$ |
| 4-$OCH_3$ | H | H | 2-Br | 4-Br | 4-Br |
| 3-Br | H | H | 2-Cl | 4-Cl | 4-Cl |
| 3-Cl | H | H | 4-Cl | 4-Cl | 4-Cl |
| 2-F | H | H | 4-$CH_3$ | 3-$OCH_3$ | 3-$OCH_3$ |
| 2-$OCH_3$ | H | H | 3-$OCH_3$ | 3-$OCH_3$ | 3-$OCH_3$ |
| 4-$CH_3$ | H | H | 4-F | 4-F | 4-$C_6H_5$ |
| 4-n-$C_4H_9$ | H | H | 4-$CH_3$ | 4-$CH_3$ | 4-$CH_3$ |
| 3-O-n-$C_4H_9$ | H | H | 4-$C_6H_5$ | 4-$C_6H_5$ | 4-$C_6H_5$ |
| 2-$OC_2H_5$ | H | H | 3-$C_6H_5$ | H | H |
| 4-n-$C_3H_7$ | H | H | 3-$CH_3$ | H | H |
| 3-Cl | 3-Cl | H | 3-F | H | H |
| 4-Cl | 4-Cl | H | 4-t-$C_4H_9$ | 4-t-$C_4H_9$ | 4-t-$C_4H_9$ |

Those substituted triphenylmethyl chlorides not described in the literature are prepared by reaction of the appropriate benzophenone with a Grignard reagent of an appropriately substituted bromobenzene, e.g. m-fluoro bromobenzene in the manner described in J. Chem. Soc. 4257–62 (1957).

The protecting groups are removed by the method of Example 2.

EXAMPLE 12

6-(Diphenyl-[2-methylphenyl]Methylamino)-2,2-Dimethyl-3-(5-Tetrazolyl) penam

Finely ground sodium azide (325 mg., 5 mmoles) is added to a solution of 6-(diphenyl-[2-methylphenyl]methylamino)-2,2-dimethyl-3-cyanopenam (45.4 mg., 1 mmole) in ethanol-free chloroform (5 ml.) containing (271 mg., 2 mmoles) of N-methylpiperidine hydrochloride and 5 drops of N-methylpiperidine. The mixture is heated to reflux for one hour after which a second equivalent of N-methyl-piperidine hydrochloride is added. Refluxing is continued for another hour. The reaction mixture is allowed to stand at room temperature overnight. Chloroform (15 ml.) is added followed by water (at pH 2.5) (15 ml.). The mixture is agitated, the water phase separated and the water wash repeated four more times. The chloroform phase is dried ($MgSO_4$) and evaporated under reduced pressure to give a foam. Yield 25%; 124 mg.

The NMR spectrum (in $CDCl_3$) shows absorption bands at 1.0 + 1.60 (2s, 3H each, C-2 methyls), 1.97 (s, 3H, AR-$CH_3$), 3.04 (d, J=11 $H_z$, 1H, NH), 4.40 + 4.67 (m, 2H, $H_5$ + $H_6$), 5.17 (s, 1H, $H_3$) and 7.16 (m, 14H aromatic protons) ppm.

In like manner the remaining products of Example 2 and those of Examples 10 and 11 are converted to corresponding 6-(N-protected amino)-2,2-dimethyl-3-(5-tetrazolyl)penams.

EXAMPLE 13

6-Triphenylmethylamino-2,2-Dimethyl-3-(5-Tetrazolyl)penam

A mixture of 6-triphenylmethylamino-2,2-dimethyl-3-cyanopenam (5.58g., 12.7 mmoles), N-methylpiperidine hydrochloride (1.72g., 12.7 mmoles), sodium azide (826 mg., 12.7 mmoles) and dioxane (150 ml.) is heated at reflux for fifteen hours. The brown reaction mixture is concentrated under reduced pressure to a dark brown sludge. The sludge is chromatographed on a silica gel (70–230 mesh) column (38.1 × 44.45 cm.) using chloroform- 10% methanol as eluant. Fractions (60 ml. each) are collected. The title product is eluted in fractions 12–50 and is recovered therefrom by concentration under reduced pressure to a tacky orange-brown oil. (The oil is triturated in chloroform and the resulting white crystals filtered and washed with chloroform (830mg., 13.6%).

It is purified further by dissolution in a minimium volume of warm acetone followed by addition of 1.5 volumes of hexane and chilling. The white crystalline product is filtered, washed with hexane and dried in vacuo at 56° C. for 4 hours. (780 mg. of crude gives 513 mg. of purified product M.P. 118° C. (dec.). NMR and quantitative analysis indicate the product is obtained as a hemi-hydrate, apparently as a result of water in the reactants and solvents.

The NMR spectrum (in DMSO-$D_6$) shows absorption bands at .92 + 1.60 (2s, 3H each, C-2 methyls), 3.35 (d, J=ca, 11 $H_z$, 1H, NH), 4.48 + 4.68 (m, 2H, $H_5$ + $H_6$), 5.32 (s, 1H, $H_3$), 6.15 (s, 1H, tetrazole-NH), 7.10–7.80 (m, 15H, aromatics) ppm.

EXAMPLE 14

6-Triphenylmethylamino-2,2-Dimethyl-3-(5-Tetrazolyl)Penam

A mixture of 6-triphenylmethylamino-2,2-dimethyl-3-cyanopenam benzene solvate, (258 mg., 0.5 mmole), sodium azide (33 mg. 0.5 mmole), triethylamine hydrochloride (69 mg., 0.5 mmole) and chloroform (10 ml.) is stirred and heated to reflux for three hours. Sodium azide (0.5 mmole) is then added to the mixture and refluxing continued overnight. One equivalent of each of sodium azide and triethylamine hydrochloride are added to the mixture is refluxed for an additional two hours. These additions are repeated twice more after which the mixture is again refluxed overnight. The mixture is cooled to room temperature and chloroform (10 ml.) added followed by water (10 ml.). The pH is adjusted to 2.0 with 6N hydrochloric acid, the mixture thoroughly mixed and the layers separated. The chloroform phase is washed with water (10 ml.) and is then seeded with a crystal from the product of Example 13. Crystallization occurs within five minutes. The slurry is stirred for ten minutes and then slowly added to an equal volume of hexane. The resulting slurry is stirred for 15 minutes and then filtered. The filter cake is washed with hexane and then air dried. Yield = 124 mg., 51.5%.

The NMR spectrum (in DMSO-D$_6$) shows absorption bands of this compound identical to those of Example 13.

EXAMPLE 15

6-Triphenylmethylamino-2,2-Dimethyl-3-(5-Tetrazolyl)penam

A mixture of dry N-methylpiperidine hydrochloride (8.14 g., 0.06 mole) anhydrous ethanol free chloroform (180 ml.), 6-triphenylmethylamino-2,2-dimethyl-3-cyanopenam (13.2g., 0.03 mole), finely powdered sodium azide (3.9 g., 0.06 mole) and N-methylpiperidine (8.9 g., 0.09 mole) is heated to 53° C. (internal temperature) for 80 minutes. It is then cooled to room temperature and diluted with ethanol free chloroform (750 ml.) and water (800 ml.). It is thoroughly shaken, the chloroform phase separated and washed successively with 1.5N HCl (1 × 1000 ml.) and water (1 × 800 ml.). The chloroform solution is filtered through anhydrous sodium sulfate and then concentrated under reduced pressure to about 300 ml. White crystals separate. The concentrate is diluted with hexane (350 ml.) and filtered after 15 minutes. The crystalline product is washed with hexane and dried in air for 15 minutes followed by drying under vacuum at 56° C. for 1 hour. Yield = 7.66 g. (52.9%).

The NMR spectrum (in DMSO-D$_6$) shows absorption bands of this compound identical to those of Example 13.

EXAMPLE 16

6-Triphenylmethylamino-2,2-Dimethyl-3-(5-Tetrazolyl)penam

A mixture of 6-triphenylmethylamino-2,2-dimethyl-3-cyanopenam (4.39 g. 0.01 mole), anhydrous ethanol-free chloroform (20 ml.), powdered sodium azide (650 mg., 0.01 mole) and dry N-methylpiperidine (2.98 g., 0.03 mole) is heated to 58°-60° C. (internal temperature). To the mixture is added with stirring 5 ml. of a solution of dry N-methylpiperidine hydrochloride (1.5 g., 0.011 mole) in ethanol-free chloroform (20 ml.) every 15 minutes over a period of one hour. The mixture is stirred and heated for 1.5 hours at 58°-60° C. following the additions of N-methylpiperidine and is then charged with finely powdered sodium azide (650 mg.) and N-methylpiperidine hydrochloride (1.5 g., 0.011 mole) in ethanol-free chloroform (20 ml.). The reaction mixture is heated for an additional hour and is then cooled to room temperature and diluted with water (150 ml.) and ethanol-free chloroform (250 ml.). The mixture is thoroughly shaken and the chloroform phase then separated and washed with successively with 1N HCl (1 × 250 ml.) and water (1 × 150 ml.).

The chloroform solution is filtered through anhydrous sodium sulfate and the concentrated in vacuo to about 100 ml. volume whereupon some crystals separate. The concentrate is diluted with hexane (150 ml.) and is filtered after 20 minutes. The crystalline product is washed with 50 ml. of a 1:1 chloroform: hexane solution. It is air dried further in a vacuum oven at 40° C. for one hour. Yield = 2.93 g. of white crystals (60.7%). M.P. 133°-137° C. (dec.).

The NMR spectrum (in DMSO-D$_6$) shows absorption bands of this compound identical to those of Example 13.

EXAMPLE 17

6-Triphenylmethylamino-2,2-Dimethyl-3-(5-Tetrazolyl)Penam

A mixture of 6-triphenylmethylamino-2,2-dimethyl-3-cyanopenam (10 g. 0.0193 mole) sodium azide (7.41 g., 0.114 mole), N-methylpiperidine hydrochloride (3.39 g., 0.025 mole) and chloroform (100 ml.) is refluxed for four hours in a round-bottomed flask equipped with stirrer, condenser, and drying tube. The reaction mixture is then cooled and water (300 ml.) and chloroform (100 ml.) added. The mixture is thoroughly mixed, the chloroform layer separated and washed successively with 1N hydrochloric acid (100 ml.) and saturated brine (100 ml.). It is then filtered quickly through anhydrous sodium sulfate and concentrated under reduced pressure to about 75 ml. Hexane (20 ml.) is added to the concentrate to precipitate the product as white crystals. The crystals are recovered by filtration, washed with 20% hexane-methylene chloride (50 ml.) and dried in vacuo at room temperature. Yield = 2.7 g. (29.6%) m.p. 133°-136° C.

The NMR spectrum (in DMSO-D$_6$) shows absorption bands of this compound identical to those of Example 13.

EXAMPLE 18

6-(2-Phenylacetamido)-2,2-Dimethyl-3-(5-Tetrazolyl)Penam

A mixture of p-toluenesulfonic acid monohydrate (788 mg., 4.14 mmoles), acetone (35 ml.) and 6-triphenylmethylamino-2,2-dimethyl-3-(5-tetrazolyl)penam (2.0 g.,) 4.14 mmoles) is stirred for twenty minutes at room temperature and is then diluted with water (100 ml.) and isopropylether (100 ml.). The biphasic mixture is stirred vigorously and adjusted to pH 7 with 2N sodium hydroxide. Phenylacetyl chloride (700 mg., 4.55 mmoles freshly distilled) is added and the reaction mixture maintained at pH between 5.5-6.5 by addition of 2N sodium hydroxide as necessary. Reaction is continued until the pH levels off at 6.5. The two phases are separated and the aqueous phase washed with ether (2 × 50 ml.). It is then layered with chloroform (100 ml.) and adjusted to pH 2 by addition of 6N HCl. The mixture is stirred, the phases separated and the aqueous phase extracted with chloroform (2 × 50 ml.). The chloroform phases are combined, dried (Na$_2$SO$_4$), and then concentrated under reduced pressure to about 50 ml. volume. A 1:1 solution of ether-hexane is added dropwise with vigorous stirring to the concentrate until precipitation of the product is complete. The white precipitate is filtered and air-dried. Yield = 850 mg. (57.4%) m.p. 168°-170°;

The NMR spectrum (in DMSO-D$_6$) shows absorption bands at 1.10 + 1.68 (2s, 3H each, C-2 methyls), 3.60 (s, 2H, φ-CH$_2$), 5.28 (s, 1H, H$_3$), 5.42-5.80 (m, 2H, H$_5$ + H$_6$ and 7.30 (s, 5H, aromatic protons)ppm.

EXAMPLE 19

6-Amino-2,2-Dimethyl-3-(5-Tetrazolyl)penam

To a slurry of dry acetone (5 ml.) and 6-triphenylmethylamino-2,2-dimethyl-3-(5-tetrazolyl)penam (483 mg., 1.0 mmole) at room temperature is added p-toluenesulfonic acid monohydrate (209 mg., 1.1 mmole). The resulting solution is stirred for 10 minutes and then ether (30 ml.) is added over a five minute period. The mixture is stirred for ten minutes after which the solvent is decanted from the tacky solid. The solid is dissolved in tetrahydrofuran (30 ml.) and placed on a column (300 × 6 mm.) packed with 10 g. of Florisil (synthetic magnesium silicate). The column is washed with tetrahydrofuran until a total of 125 ml. is collected. The eluate is concentrated to dryness under reduced pressure at 40° C. to give 210 mg. of solid. The solid is slurried in ether (30 ml.), filtered, washed with ether and air-dried. Yield = 121 mg. (50%).

The NMR spectrum (in DMSO-D$_6$) shows absorption bands at 1.08 + 1.59 (2s, 3H each, C-2 methyls), 4.60 + 5.52 (2d, J = 4.0 H$_z$, 2H, H$_5$ + H$_6$), 5.10 (s, 1H H$_3$) and 5.88 (s, 3H, NH$_3$)ppm.

EXAMPLE 20

6-Amino-2,2-Dimethyl-3-(5-Tetrazolyl)Penam Tosylate

Following the procedure of Example 2, the triphenylmethyl and substituted triphenylmethyl derivatives of Examples 12-17 are converted to the title product by reaction with p-toluenesulfonic acid.

The use of other acids in place of p-toluenesulfonic acid also detritylates the products of Examples 12-17 but, of course, produces the acid salt of 6-amino-2,2-dimethyl-3-(5-tetrazolyl)penam corresponding to the acid used; e.g., benzenesulfonic acid, methanesulfonic acid, hydrogen chloride, hydrogen bromide, trifluoroacetic acid, chloroacetic acid, acetic acid.

EXAMPLE 21

To a solution of anhydrous penicillin G amide (3.6 g., 0.0108 mole) and quinoline (6.97 g., 0.054 mole) in deuterochloroform (50 ml.) at −5° C. is added phosphorous pentachloride (5.05 g., 0.0243 mole) in one portion. The reaction mixture is stirred at −5° C. for a half-hour and is then allowed to warm to room temperature. A nuclear magnetic resonance spectrum of the mixture indicated complete formation of 6-(1-chloro-2-phenylethylideneimino)-2,2-dimethyl-3-cyanopenam. Absorption bands occurred at 1.54 + 1.72 (S, 3H each, C-2 methyls); 3.98 (S, 2H,

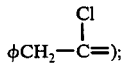

4.79 (S, 1H, H$_3$); 5.25–5.70 (m, 2H, H$_5$ + H$_2$); 7.35 (S, 5H, φ).

The reaction mixture is recooled to −5° C. and treated with dry n-propanol (7.8 ml.) and the resulting mixture stirred for one hour. An NMR scan of the reaction mixture shows the imino chloride β-lactam protons have disappeared and are replaced with a new group of protons assignable to the corresponding imino ether. Treatment of the reaction mixture with water (1 ml.) results in precipitation of 6-amino-2,2-dimethyl-3-cyanopenam hydrochloride (1.60 g., 64% yield).

EXAMPLE 22

6-(2-Phenoxyacetamido)-2,2-Dimethyl-3-(5-Tetrazolyl)Penam

A stirred slurry of 6-amino-2,2-dimethyl-3-(5-tetrazolyl)penam (480 mg.) in water (10 ml.) is cooled to 0° C., and then the pH is adjusted to 8.0 using 1N sodium hydroxide. To this solution is then added phenoxyacetyl chloride, (0.25 ml.) in portions, with the pH of the solution being maintained between 7 and 8 during the addition, using 0.1N sodium hydroxide. The solution is stirred a further 30 minutes at 0° C. at pH 8. It is then extracted with chloroform, and the extracts are discarded. The aqueous phase is acidified to pH 2 with dilute hydrochloric acid, and then it is further extracted with chloroform. The latter extracts are dried using calcium sulfate and then evaporated in vacuo to give the crude product as a gummy solid. This is purified by dissolving it in chloroform (20 ml.), and adding the resultant solution dropwise to hexane (250 ml.). The precipitate which forms is filtered off, giving 385 mg. of 6-(2-phenoxyacetamido)-2,2-dimethyl-3-(5-tetrazolyl)penam as a white amorphous solid. The infrared spectrum (KBr disc) of the product shows absorption bands at 1785 cm$^{-1}$ (β-lactam carbonyl), 1670 cm$^{-1}$ (amide I band) and 1540 cm$^{-1}$ (amide II band). The NMR spectrum (in DMSO-d$_6$) shows absorption bands at 7.50–6.70 ppm (multiplet, aromatic hydrogens), 5.70 ppm (multiplet, C-5 and C-6 hydrogens), 5.35 ppm (singlet, C-3 methyl hydrogens), 4.66 ppm (s, 2, φ-OCH$_2$) and 1.66 + 1.16 (s, 3H each, C-2 methyls)ppm.

Its in vitro antibacterial activity expressed as minimum inhibitory concentration (MIC) in mg./ml. against a strain of Stretocuccus pyogenes is <0.1.

EXAMPLE 23

6-(2-Phenylacetamido)-2,2-Dimethyl-3-(5-Tetrazolyl)Penam

Repetition of the procedure of Example 22, but using an equivalent amount of phenylacetyl chloride as acylating agent in place of phenoxyacetyl chloride provides the title compound. Its MIC (mg./ml.) versus Streptococcus pyogenes is <0.1.

EXAMPLE 24

6-(D-2-Amino-2-Phenylacetamido)-2,2-Dimethyl-3-(5-Tetrazolyl)Penam

A stirred suspension of 6-amino-2,2-dimethyl-3-(5-tetrazolyl)penam (200 mg.) in water (5 ml.) is cooled to 0°–5° C. in an ice-bath. The pH is then adjusted to 7.0 using dilute sodium hydroxide solution. At this point, D-2-amino-2-phenylacetyl chloride hydrochloride (274 mg., Hardcastle et al., Journal of Organic Chemistry, 31, 897 [1966]) is added portionwise during 15 minutes at 0°–5° C., and with the pH maintained between 6 and 7 by the addition of dilute sodium hydroxide. At the end of the addition, the reaction mixture is stirred for a further 15 minutes and then filtered. The pH of the mother liquors is adjusted to 4.4 with dilute hydrochloric acid, and then the solution is stored overnight in the refrigerator. The solution is then filtered, and the mother liquors are placed on a column of 25 g. of Sephadex LH-20 (Pharmacia Fin Chemicals, Inc.) made up in water. The column is eluted with water, taking fractions, and the composition of the fractions is assayed by thin-layer chromatography. The fractions containing the pure product are combined, and evaporated under high vacuum to a volume of approximately 1 ml. After this solution has been set aside for a short period, the product crystallizes out. It is filtered off, washed briefly with water and dried. The yield is 55 mg. of pure 6-(D-2-amino-2-phenylacetamido)-2,2-dimethyl-3-(5-tetrazolyl)penam, m.p. 192°–196° C. The infrared spectrum (KBr disc) shows absorptions at 1770 cm$^{-1}$(β-lactam carbonyl), 1680 cm$^{-1}$ (amide I band) and 1520 cm$^{-1}$ (amide II band).

MIC (mg./ml.) versus *Streptocuccus pyogenes* is <0.1.

EXAMPLE 25

The procedure of Example 1 is repeated but using the appropriate substituted trityl chloride in place of trityl chloride to provide the following compounds:

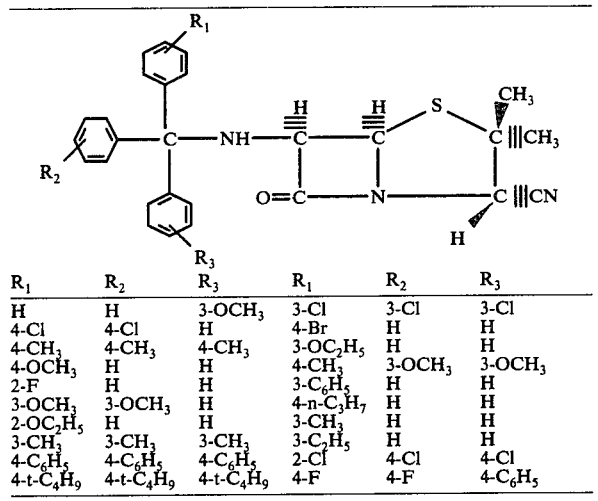

| R$_1$ | R$_2$ | R$_3$ | R$_1$ | R$_2$ | R$_3$ |
|---|---|---|---|---|---|
| H | H | 3-OCH$_3$ | 3-Cl | 3-Cl | 3-Cl |
| 4-Cl | 4-Cl | H | 4-Br | H | H |
| 4-CH$_3$ | 4-CH$_3$ | 4-CH$_3$ | 3-OC$_2$H$_5$ | H | H |
| 4-OCH$_3$ | H | H | 4-CH$_3$ | 3-OCH$_3$ | 3-OCH$_3$ |
| 2-F | H | H | 3-C$_6$H$_5$ | H | H |
| 3-OCH$_3$ | 3-OCH$_3$ | H | 4-n-C$_3$H$_7$ | H | H |
| 2-OC$_2$H$_5$ | H | H | 3-CH$_3$ | H | H |
| 3-CH$_3$ | 3-CH$_3$ | 3-CH$_3$ | 3-C$_2$H$_5$ | H | H |
| 4-C$_6$H$_5$ | 4-C$_6$H$_5$ | 4-C$_6$H$_5$ | 2-Cl | 4-Cl | 4-Cl |
| 4-t-C$_4$H$_9$ | 4-t-C$_4$H$_9$ | 4-t-C$_4$H$_9$ | 4-F | 4-F | 4-C$_6$H$_5$ |

EXAMPLE 26

6-Triphenylmethylamino-2,2-Dimethyl-3-Cyanopenam

A mixture of 6-triphenylmethylamino-2,2-dimethyl-3-carbamylpenam (11.01 g., 0.024 mole), dry pyridine (4.9 g., 0.062 mole) and dry chloroform (250 ml.) is stirred for five minutes and the resulting solution cooled to 0° C. in a wet ice/acetone bath. Phosgene (8.8 ml. of 3.41 molar solution in chloroform) is added by means of a syringe. The reaction mixture is stirred at 5° C. for ten minutes after which the cooling bath is removed and the reaction mixture allowed to warm to room temperature. It is stirred for 30 minutes and then washed successively with water (300 ml.), 1N hydrochloric acid (300 ml.), and water (300 ml.). The chloroform solution is dried (MgSO$_4$), treated with activated charcoal, and filtered through diatomaceous earth. The filtrate is concentrated to reduced pressure and the residue taken up in methylene chloride (450 ml.). The methylene chloride solution is washed successively with 1N hydrochloric acid (150 ml.) and water (300 ml.) and then dried using anhydrous sodium sulfate. The dried solution is then filtered and concentrated under reduced pressure to give the product as a golden foam (7.1 g., 67.3%).

It is purified by the procedure of Example 7.

EXAMPLE 27

6-Triphenylmethylamino-2,2-Dimethyl-3-Cyanopenam

A mixture of 6-triphenylmethylamino-2,2-dimethyl-3-carbamylpenam (11.01 g., 0.024 mole), dry pyridine (5.6., 0.072 mole) and dry chloroform (40 ml.) is stirred for five minutes and the resulting solution cooled to 0° C. in a wet ice/acetone bath. Phosphorous pentachloride (8 g.) is added and the reaction mixture is stirred at 0°–5° C. for 10 minutes after which the cooling bath is removed and the reaction mixture allowed to warm to room temperature. It is stirred for 90 minutes and then phosphorous pentachloride (2 g.) added and stirring continued for another 90 minutes. The reaction mixture is added to water (320 ml.) and the mixture washed successively with 1N hydrochloric acid (320 ml.), and water (320 ml.). The chloroform solution is dried (MgSO$_4$), treated with activated charcoal, and filtered through diatomaceous earth. The filtrate is concentrated to reduced pressure and the residue taken up in methylene chloride (250 ml.). The methylene chloride solution is washed successively with 1N hydrochloric acid (150 ml.) and water (250 ml.) and then dried. The dried solution is then filtered and concentrated under reduced pressure to give the product as a golden foam (6.33 g., 60%).

It is purified by the procedure of Example 7.

What is claimed is:

1. A compound selected from the group consisting of (a) those of the formula

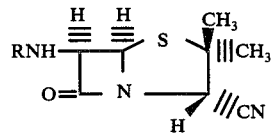

wherein R is selected from the group consisting of hydrogen and the group of the formula wherein each of R$_1$, R$_2$ and R$_3$ is selected from the group consisting of hydrogen, chloro, bromo, fluoro, alkyl having from 1 to 4 carbon atoms, alkoxy having from 1 to 4 carbon atoms and phenyl and (b) the acid addition salts of those compounds wherein R is hydrogen.

2. The compound of claim 1 wherein R is hydrogen.

3. The compound of claim 1 wherein R is the group of said formula.

4. The compound of claim 3 wherein R$_1$, R$_2$ and R$_3$ are each hydrogen.

* * * * *